US006258078B1

(12) United States Patent
Thilly

(10) Patent No.: US 6,258,078 B1
(45) Date of Patent: Jul. 10, 2001

(54) LUER CONNECTOR WITH ROTATIONALLY ENGAGING PIERCING LUER

(75) Inventor: Jacques Thilly, Brussels (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/341,934

(22) PCT Filed: Jan. 16, 1998

(86) PCT No.: PCT/EP98/00385

§ 371 Date: Jul. 20, 1999

§ 102(e) Date: Jul. 20, 1999

(87) PCT Pub. No.: WO98/32411

PCT Pub. Date: Jul. 30, 1998

(30) Foreign Application Priority Data

Jan. 20, 1997 (GB) .................................................. 9701413

(51) Int. Cl.[7] .............................. A61M 5/32; A61M 5/24; A61B 19/00; B65D 83/10

(52) U.S. Cl. .......................... 604/411; 604/905; 604/256; 604/415; 604/201; 604/86; 215/247; 206/363; 206/365; 206/364

(58) Field of Search .................................... 604/200, 201, 604/86–89, 403, 411, 414, 415, 905, 256; 215/247, DIG. 3; 206/363, 365, 364

(56) References Cited

U.S. PATENT DOCUMENTS

| | | | | |
|---|---|---|---|---|
| 3,884,229 | * | 5/1975 | Raines et al. . | |
| 3,977,555 | * | 8/1976 | Larson | 215/247 |
| 4,084,588 | | 4/1978 | Koenig | 128/218 R |
| 5,024,256 | | 6/1991 | Vadher | 141/329 |
| 5,501,676 | * | 3/1996 | Niedospial et al. | 604/283 |
| 6,070,623 | * | 6/2000 | Aneas | 141/329 |

FOREIGN PATENT DOCUMENTS

| | | |
|---|---|---|
| 0 126 718 | 11/1984 | (EP) . |
| 2 256 752 | 8/1975 | (FR) . |

* cited by examiner

*Primary Examiner*—Angela D. Sykes
*Assistant Examiner*—Ron Harris, Jr.
(74) *Attorney, Agent, or Firm*—Zoltan Kerekes; Stephen Venetianer; Charles M. Kinzig

(57) ABSTRACT

A luer connector which facilitates connection of a hypodermic syringe to the vial, comprising a luer connectable to a syringe and which extends to a sharpened end capable of being driven through a puncturable vial closure to thereby puncture the closure; a luer support, mountable on a vial, and which initially supports the luer in a first position in which the sharpened end of the conduit is pointed toward the closure; a luer driver such that movement of the driver relative to the support causes the luer to be driven so that the sharpened end punctures the closure and enters the vial.

12 Claims, 6 Drawing Sheets

LUER CONNECTOR WITH ROTATIONALLY ENGAGING PIERCING LUER

CROSS-REFERENCE TO RELATED APPLICATIONS

This application is a 371 of International Application Number PCT/EP98/00385, filed on Jan. 16, 1998.

STATEMENT REGARDING FEDERALLY SPONSORED RESEARCH OR DEVELOPMENT

Not applicable.

BACKGROUND OF THE INVENTION

1. Field of the Invention

This invention relates to luer connectors.

Luer connectors are devices for enabling a connection to be made between the nozzle of a hypodermic syringe and the interior of a pharmaceutical vial through a puncturable rubber closure, so that for example water can be introduced into such a vial to reconstitute a drug substance within the vial, and the reconstituted solution of drug substance can be subsequently sucked out of the vial via the luer connector into the body of the syringe. The nozzle of the syringe may then be detached from the luer connector and a hypodermic needle attached to the syringe nozzle. The luer connector therefore avoids the need to insert a hypodermic needle through the closure and facilitates a sterile connection between the syringe and the vial. Luer connectors generally comprise a luer port, i.e. a small female port into which the syringe nozzle can be inserted, connected to a tubular conduit with a sharpened end which can be driven through the rubber vial closure.

2. Description of the Related Art

A number of luer connectors are known, for example that disclosed in WO 97/10156, which is mounted upon a vial and requires the nozzle of the syringe to be inserted into its luer lock and the body of the syringe to be then used as a driver to drive the sharpened end of its conduit through the vial closure. This can cause premature operation of the syringe during the driving operation. Other constructions of luer connector are disclosed in U.S. Pat. No. 530372, EP 0351643A and EP 0587347A.

BRIEF SUMMARY OF THE INVENTION

It is an object of this invention to provide an improved luer connector.

DETAILED DESCRIPTION OF THE INVENTION

According to this invention a luer connector comprises;

a luer comprising a luer port connectable to a syringe and being in communication with a first end of a channel passing longitudinally through a tubular conduit, the conduit extending longitudinally from the luer port to a second end of the channel, the end of the tubular conduit remote from the luer port being sharpened so as to be capable of being driven through a puncturable vial closure to thereby puncture the closure;

a luer support, mountable on a vial when the vial is sealed with a puncturable vial closure, the support initially supporting the luer longitudinally moveable in a first position in which the sharpened end of the conduit is pointed toward the closure;

a luer driver, mounted on the support and moveable relative to the support, the luer and driver having respective engagement parts such that movement of the driver relative to the support causes the engagement part(s) of the driver to bear upon the engagement part(s) of the luer so as to drive the luer longitudinally into a second position in which the sharpened end of the conduit is driven through the closure to puncture the closure and to enter the vial.

The luer port may be of essentially conventional type comprising a small female port suitable for male-female engagement with the nozzle of a conventional hypodermic syringe. The luer may be provided with features, e.g. a connection for an adapter, to enable the luer to be locked to a hypodermic syringe to minimise the risk of accidental disconnection.

The luer port and the conduit may be of integral construction, e.g. the conduit being an integral extension of the port, and the port and conduit may be made of plastics materials. Alternatively the luer port and conduit may be made separately and may be connected together. For example the conduit may be made of metal, e.g. in the form of a steel needle, and the luer port may be made of plastics material, the port and conduit being bonded together e.g. by adhesive or by moulding the luer port around the metal conduit. The use of a sharpened metal rather than a plastics material, conduit may allow the use of lower puncturing force. The sharpened end of the channel may be of any conventionally sharpened shape known for such conduits on known luers. The channel may conveniently open sideways out of the sharpened end of the conduit to allow the conduit to have a sharp point.

The luer support may comprise a sleeve which is mountable e.g. by a snap-fit, screw fit, friction fit etc., or other methods apparent to those skilled in the art, around the neck of the vial, so as to be thereby retained on the neck. As most conventional vials have an enlarged bead around their mouth opening a snap-fit over this bead is a convenient way by means of which the sleeve may be mounted on the vial. By such means the support may be mounted in a way on the neck of the vial which does not allow it to rotate, or move longitudinally, or otherwise move on the neck of the vial. There are known means for mounting such a support in the form of a sleeve on a vial. For example one known means is that used in the COMAR™ "Harmony"™ system in which the sleeve and the neck of the vial are provided with co-operating "gear teeth" type structures which engage and prevent relative rotation, whilst a snap-fit engaging groove and bead on the sleeve and vial neck respectively prevent longitudinal detachment of the sleeve from the vial neck. For example another known means is resilient longitudinally extending fingers on the sleeve which grip around a bead on the neck of the vial, the fingers being locked into this position by means of a restraining collar around the fingers. A system of this type is disclosed in inter alia WO 97/10156 and is also used commercially in the LYO-JECT™ system supplied by Vetter Injekt System GmbH.

When mounted on the vial the support suitably extends above the mouth of the vial (directions are defined relative to the bottom of the vial when this is stood upright, although it is to be understood that the luer connector of the invention is useable with the vial in other orientations, e.g. with its mouth downwards) and may include a part, e.g. internal flange or rim parts, which bear upon the puncturable closure and help to hold the closure in place, for example compressing the closure down toward the lip of the mouth of the vial. Such flange or rim parts suitably include a central aperture to allow the sharpened end of the luer to pass through the closure. This central aperture may be sealed with a puncturable sealing membrane, which may be integral with (e.g.

being a thin film of the support material) or may be attached to the flange or rim parts.

When mounted on the vial the upper part of the support above the mouth of the vial may form a guide for the luer, for example in the form of a generally tubular e.g. cylindrical extension defining a compartment extending above the vial closure, of suitable dimensions that the luer can be supported therein in its first position with the sharpened end of the conduit pointed toward the closure. Within such a cylindrical compartment the luer may be supported with its longitudinal axis e.g the axis of its channel and/or conduit coaxial with the cylindrical axis. In the first position of the luer the sharpened end may be in non-puncturing contact with the upper surface of the closure or distanced from it. Suitably the inner surfaces of the compartment and facing parts of the outer surface of the luer may include guides, e.g. cooperating projections and longitudinal grooves or slots so that as the luer is driven from its first position to its second position its movement is guided so as to be smooth and with the minimum amount of deviation from a non longitudinal path. For example the guides may comprise a plurality of longitudinally extending slots on the support into which corresponding projections, e.g. in the form of legs or ribs etc. from the luer fit and within which they may move longitudinally. Alternatively the projections may be on the luer driver and the slots or grooves on the luer. As discussed in more detail below such guides may also serve to prevent the luer from rotating relative to the support.

The luer is suitably provided with one or more abutment part(s) which when the luer has reached the extreme end of its movement into the second position, i.e. the conduit has entered the vial as far as is desired, abut against the closure and/or the support to prevent further longitudinal movement. Such abutment parts may suitably comprise a flange or part flange, or legs etc. extending radially from the outer surface of the conduit, and a corresponding flange, rim part, bulkhead wall, legs etc. at the lower extremity of the compartment. In such a construction, when the luer reaches the lower limits of its travel within the compartment, e.g. its second position, the two said respective abutment surfaces abut to prevent further downward motion of the luer.

The luer and the support may also include respective engagement parts so that when the luer has reached the limits of its movement from its first to its second position, with the conduit as far within the vial as desired, the luer is locked in place in its second position. For example the inner surface of the support and the outer surface of the luer may be provided with snap-fit engaging parts which lock together when the luer is in its second position. Such parts may also comprise or be mounted on the above-mentioned abutment parts, or may be located on other parts of the device.

The luer driver is mounted on the support so as to be capable of having a driving force applied to it by a user, and as a consequence the luer driver transmits longitudinal force to the luer so as to drive the luer from its first to its second position so that the closure is punctured. The luer driver may be initially moveable relative to both the support and the luer, such that movement of the luer driver relative to the luer under the action of driving force brings their respective engagement parts into engagement.

In a preferred construction the luer driver is rotatable relative to the support and luer, for example by means of a hand-twisting action, and the respective engagement means on the luer and driver comprise engaging screw thread parts such that engagement of the screw thread parts on the said rotational movement causes the luer to be screwed downwards toward the second position. In such a construction parts of the driver are constructed and arranged to be gripped by the user and rotated, and such parts may advantageously be provided with grip-enhancing features, e.g. external ribs or a knurled surface etc.

For example the driver may comprise a cylindrical sleeve or part sleeve, coaxial with an upper part of the support which is in the form of a cylindrical compartment as described above, and being able to rotate coaxialy on the upper part of the support. Suitably such a driver may surround such an upper part in the manner of a surrounding sleeve or skirt. Alternatively the luer driver may be within and surrounded by the support, and the support may in such a construction be in the form of a sleeve surrounding the luer driver. The luer driver may suitably be in the form of a closure, e.g. a cap closing the upper end of the compartment, e.g. having a wholly or partly closed end over the compartment when the driver is in place. Such a cap can help to provide a sterile seal of the compartment. The sleeves of the support and driver may fit closely but slideably moveable together, also helping to provide a sterile seal between the support and driver. When the driver is in the form of such a cap the user can conveniently apply hand force to the driver without any hand contact with the luer enclosed within the compartment, thereby avoiding contamination. The above mentioned sealing membrane which closes the opening in the rim or flange parts of the support may further contribute to the sterile sealing of the compartment. Additional sterile seals may be provided at other parts of the construction, advantageously providing several lines of seals.

The screw thread parts may be a whole or part screw thread, or a screw thread on one of the driver and the luer and a projection capable of engaging with the screw thread on the other. Suitable screw thread structures will be apparent to those skilled in the art. For example when the luer driver is in the above-described form a screw thread or partial screw thread may be located on an internal surface of the sleeve, engageable with a corresponding screw thread or partial screw thread or projection capable of engaging with the screw thread on a facing surface of the luer, e.g. of the luer port. In such a construction the luer driver may have a lower part in the form of a sleeve which surrounds and is rotatable on the support, and an upper part which includes the above-described screw thread. Alternatively a screw thread may be formed on a part of the driver which extends into the compartment in the upper part of the support. For example when the driver is in the form of a surrounding external skirt a screw thread may be formed on the inner surfaces of an internal skirt which extends axially into the compartment and surrounds the luer, and the luer may have cooperating screw thread parts of the type described above on its facing outer surface. When the driver is in the form of a cap as described above, such an inner skirt may descend axially from the said wholly or partly closed end.

When the respective engagement means on the luer and driver comprise such screw thread parts, it will generally be necessary to provide the luer with some means to resist rotation with the luer driver when the luer driver is rotated on the support so that relative rotation of the luer and the driver, and hence the screw thread action, can occur. This can be achieved by providing the luer and the support with respective cooperating parts which engage to prevent rotation. For example the above-mentioned guides which guide the luer into following a longitudinal path can also conveniently serve to achieve this. For example the luer may have parts which fit within a guide in the support that prevents such rotation, or the luer may be of a sectional shape that prevents rotation (e.g. polygonal or oval rather than circular in section), or the luer may be provided with sideways projecting legs that engage with longitudinally aligned guides, e.g. grooves in the inner surface of the support. Such legs may conveniently also comprise the above described snap-fit connecting parts which lock together when the luer is in its second position, and/or may comprise abutment parts.

In such a construction, rotation of the driver about the support and engagement of the screw thread parts on the luer and driver causes the luer to be screwed downwards from the said first position toward the second position, and causes the sharpened end of the conduit to be driven through the closure to puncture it.

When the driver is in the form of a sleeve, e.g. a cap as described above having a wholly or partly closed end over the compartment when the driver is in place it will usually be necessary to construct such a cap that it may easily be removed from the support to expose the luer port for use when the conduit has been driven through the closure. When a driver in the form of a cap is rotatable on the support to operate the above described screw thread action, it is necessary that such ease of removal of the cap is also combined in the construction with the ability to rotate without becoming accidentally detached during rotation to operate the screw thread.

This may be achieved in a preferred construction by providing the luer with abutment parts as described above, and by providing screw thread parts which are of dimensions such that when the conduit has entered the vial as far as is desired or allowed by the abutment parts the screw thread parts on the luer driver and luer are still engaged, so as that their continued relative rotation generates an upward thrust upon the luer driver to force it off the support. The support and luer driver may have their respective facing surfaces provided with engaging circumferential bead parts and a groove, which allow rotation and guide them in smooth rotation about the axis of the sleeves whilst restraining relative axial movement. Such bead parts and a groove may be constructed that the driver is detachable from the support by a snap-fit disengagement of the bead from the groove as the driver moves in the axial direction. When the luer reaches the limit of its movement continued relative rotation of the sleeves may in the way described above generates an upward force on the driver that forces the bead and groove to snap out of engagement and allows the driver to be removed axially from the support.

For example this may be achieved by a construction of the luer connector of this invention in which the luer driver and luer have respective engaging screw thread parts thereon, and in which the luer and the support are provided with respective abutment surfaces such that the lower limit of travel of the luer within the support is reached when the respective abutment surfaces abut, and in which when the luer is in its first position the respective abutment surfaces are separated by a longitudinal distance which is less than the longitudinal distance the luer driver can be moved by the screw action of the luer driver. In this construction when the abutment surfaces on the luer abuts against the abutment surface on the luer support the luer has reached the lower limit of its travel relative to the support it has not yet reached the lower limit of travel on the screw thread on the luer driver. In such a construction when the said abutment surfaces are in contact the continued rotation of the luer driver relative to the luer will force the luer driver upwards, and this can be arranged to be sufficient that the luer driver and support are forced longitudinally out of engagement with each other such that the luer driver, e.g. in the form of a cap, can be removed. Suitable relative dimensions and arrangements of the screw thread on the luer driver and support can easily be determined by experiment.

To prevent accidental or unintended relative movement of the driver and support, the support and driver may be initially connected with breakable connectors, e.g. a small spot weld or thin plastics material strips etc. (many suitable constructions will be apparent to those skilled in the art). These break when relative motion is intentionally applied to the driver to operate the device. Such connectors may also function as tamper evidence means to detect tampering.

Therefore in a preferred embodiment of the invention a luer connector comprises;

a luer, connectable to a syringe, the luer comprising a luer port in communication with a first end of a channel passing longitudinally through a tubular conduit integrally extending longitudinally from the luer port to a second end of the channel, the end of the tubular conduit remote from the luer port being sharpened so as to be capable of being driven longitudinally through a puncturable vial closure to thereby puncture the closure; a luer support, comprising a sleeve which is mountable around the neck of the vial, so as to be thereby retained on the vial when sealed with a puncturable vial closure, the support extending into an upper part above the mouth of the vial in the form of a generally cylindrical compartment extending above the vial closure and forming a guide for the luer, the compartment being of suitable dimensions that the luer is supported therein longitudinally moveable in a first position in which the sharpened end of the conduit is pointed toward the unpunctured closure;

a luer driver, mounted on the support and capable of rotational movement relative to the support and luer, the driver comprising a cylindrical sleeve or part sleeve, coaxial with the said upper part of the support, the driver being in the form of a cap over the compartment in the upper part of the support, and having a wholly or partly closed end over the compartment when the driver is in place;

the luer and driver having respective screw thread engagement parts such that engagement of the screw thread parts on the said rotational movement causes the luer to be screwed downwards toward a second position in which the sharpened end of the conduit is driven through the closure to puncture the closure and to enter the vial.

In a more preferred embodiment of the invention a luer connector comprises;

a luer, connectable to a syringe, the luer comprising a luer port in communication with a first end of a channel passing longitudinally through a tubular conduit integrally extending longitudinally from the luer port to a second end of the channel, the end of the tubular conduit remote from the luer port being sharpened so as to be capable of being driven longitudinally through a puncturable vial closure to thereby puncture the closure;

a luer support, comprising a sleeve which is mounted and engaged around the neck of the vial, so as to be thereby retained on the vial when sealed with a puncturable vial closure, the support extending into an upper part above the mouth of the vial in the form of a generally cylindrical compartment extending above the vial closure and forming a guide for the luer, the compartment being of suitable dimensions that the luer is supported therein longitudinally moveable in a first position in which the sharpened end of the conduit is pointed toward the unpunctured closure;

a luer driver, mounted on the support and capable of rotational movement relative to the support and luer, the driver comprising a cylindrical sleeve or part sleeve, coaxial with the said upper part of the support, the driver being in the form of a cap over the compartment in the upper part of the support, and having a wholly or partly closed end over the compartment when the driver is in place;

the luer and driver having respective screw thread engagement parts such that engagement of the screw thread parts on the said rotational movement causes the luer to be screwed downwards toward a second position in which the sharpened end of the conduit is driven through the closure to puncture the closure and to enter the vial;

the luer and the support being provided with respective abutment surfaces such that the lower limit of travel of the luer within the support is reached when the respective abutment surfaces abut, and in which when the luer is in its first position the respective abutment surfaces are separated by a longitudinal distance which is less than the longitudinal distance the luer driver can be moved by the screw action of the luer driver, so that when the abutment surfaces on the luer abuts against the abutment surface on the luer support the luer has reached the lower limit of its travel relative to the support it has not yet reached the lower limit of travel on the screw thread on the luer driver and the continued rotation of the luer driver relative to the luer will force the luer driver and support are forced longitudinally out of engagement with each other.

All of the component parts of the luer connector of this invention may be made of plastics materials of the same kind as are used with known luer connectors, or as mentioned above some parts such as the conduit may be made of metal such as stainless steel.

The luer connector of the invention provides the advantage that by operation of the driver the conduit of the luer can be easily and controllably driven through the closure, and if the driver is in the form of the above described cap the luer can be kept sterile throughout this operation.

In a further aspect the invention provides a luer comprising a luer port, connectable to a syringe, the port being in communication with a first end of a channel passing longitudinally through a tubular conduit integrally extending longitudinally from the luer port to a second end of the channel, the end of the tubular conduit remote from the luer port being sharpened, suitable for use in a luer connector as described above.

In a further aspect the invention provides a luer support, mountable on a vial when sealed with a puncturable vial closure, suitable for use in a luer connector as described above.

In a further aspect the invention provides a luer driver, suitable for use in a luer connector as described above.

In a further aspect the invention provides a pharmaceutical vial having a puncturable rubber closure sealing its mouth opening, mounted with a luer connector as described above.

In a further aspect the invention provides the use of a luer connector as described above in the dispensing of a pharmaceutical formulation initially contained in a pharmaceutical vial.

BRIEF DESCRIPTION OF THE DRAWINGS

The invention will now be described by way of example only with reference to the accompanying drawings which show.

DETAILED DESCRIPTION OF THE PREFERRED EMBODIMENTS

Figure 1:
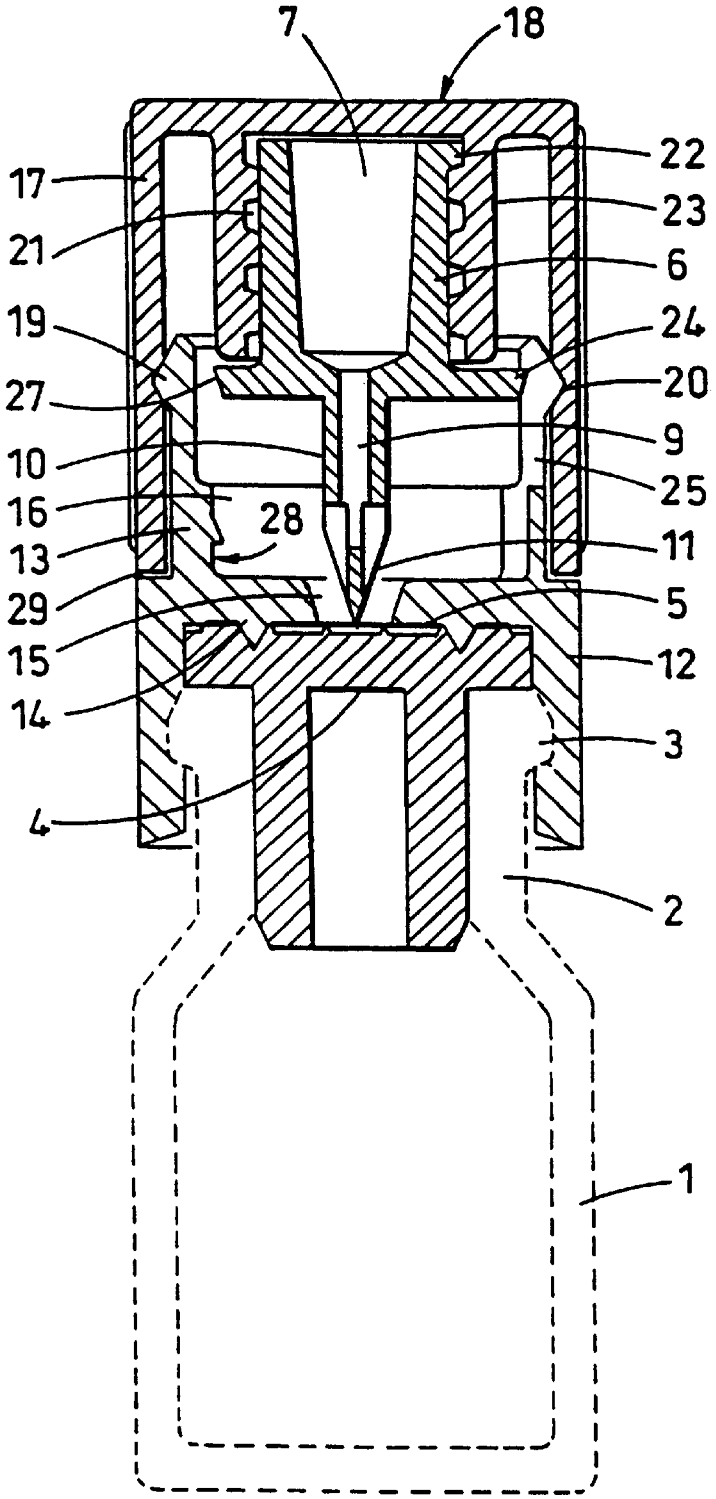
FIG. 1 shows a longitudinal section through a first type of luer connector of the invention with its luer in its first position.

Referring to FIGS. 1 to 4 a luer connector and its use is shown. A pharmaceutical vial 1 is shown, the upper part of which is formed into a neck 2, terminating in a mouth opening surrounded by an annular bead 3. The mouth opening is closed by a puncturable rubber closure 4, additionally covered by a sterility membrane 5.

The luer connector comprises a luer 6 (overall) which comprises a female luer port 7 connectable to a syringe 8, the luer port 7 being in communication with a channel 9 passing longitudinally through a tubular conduit 10, which extends longitudinally from the luer port 7, the end 11 of the tubular conduit 10 remote from the luer port 7 being sharpened so as to be capable of being driven through the central part of the puncturable vial closure 4 to thereby puncture the closure 4. The luer port 7 and the conduit 10 are of integral construction, the conduit 10 being an integral extension of the port 7.

Mounted on the neck 2 of vial 1 is a luer support 12 (overall). The luer support 12 is mountable by a snap-fit over the bead 3 around the neck 2 of the vial, so as to be thereby retained on the neck. The part of the support 12 which is mounted over the bead 3 is not shown in detail as various types of mount are available as discussed above. As shown in FIG. 1 the support holds the luer 6 longitudinally moveable in a first position in which the sharpened end 11 of the conduit 10 is pointed toward the closure 4.

The support 12 extends into an upper part 13 above the mouth of the vial and includes an internal flange 14 which bears upon the puncturable closure 4 and helps to hold the closure 4 in place, compressing the closure 4 down toward the mouth of the vial 1. The flange 14 includes a central aperture 15 to allow the sharpened end 11 of the luer to pass through the closure 4. The sterility membrane 5 is attached to the flange 4 so as to close the central aperture 15. The upper part 13 of the support also forms a generally tubular e.g. cylindrical compartment 16 extending above the vial closure 4, of suitable dimensions that the luer 6 can be supported therein in its first position with the sharpened end 11 of the conduit 10 pointed toward the closure 4. Within this cylindrical compartment the luer 6 is supported with its longitudinal axis coaxial with the cylindrical axis. In the first position of the luer 6 the sharpened end 11 is in non-puncturing contact with the upper surface of the closure 4.

Mounted on the upper part of the support is a luer driver 17 (overall) in the form of a cylindrical sleeve, coaxial with the upper part 13 of the support 12, and able to rotate coaxialy on the upper part 13 of the support 12. The driver 17 surrounds the upper part 13 in the manner of a surrounding skirt, and is in the form of a cap closing the upper end of the compartment 16 by having a wholly closed end 18 over the compartment 16. The sleeves fit closely together to provide a sterile seal between the driver 17 and compartment 16. The sleeves have their respective facing surfaces provided with engaging circumferential bead parts 19 and a groove 20, which allow relative rotation and guide the sleeves in smooth rotation about the axis of the sleeves whilst restraining relative axial movement.

The driver 17 and the luer 6 are provided with respective engagement means. These comprise engaging screw thread parts 21, 22 respectively on the driver 17 and luer 6. The screw thread parts 21, 22 comprise a whole screw thread 21 formed on the inner surfaces of an internal skirt 23 which descends axially from the closed end 18 of the driver 17 and extends axially into the compartment 16 to surrounds the luer 6, and a projection 22 on the luer 6 capable of engaging with the screw thread 21 on the internal skirt 23. Engagement of the screw thread parts 21, 22 on relative rotational movement of the driver 17 and luer 6 causes the luer 6 to be screwed downwards toward the second position as shown in FIG. 2.

The inner surfaces of the upper part 13 of the support 12 and facing parts of the outer surface of the luer 6 include guides which comprise legs 24 which project sideways from the luer 6, and engage with corresponding longitudinal slots 25 in the upper part 13 of the support 12. These legs 24 and slots 25 guide the luer 6 as it is driven longitudinally driven from its first position to its second position by the engagement of the screw thread parts 21, 22 so that the longitudinal movement of the luer 6 is smooth and with the minimum amount of deviation from a non longitudinal path.

It is necessary to provide the luer 6 with means to resist rotation when the driver 17 is rotated on the support 12 so that relative rotation of the luer and the driver, and hence the screw thread action, can occur. This is achieved by the engagement of the legs 24 and the slots 25.

Figure 2:
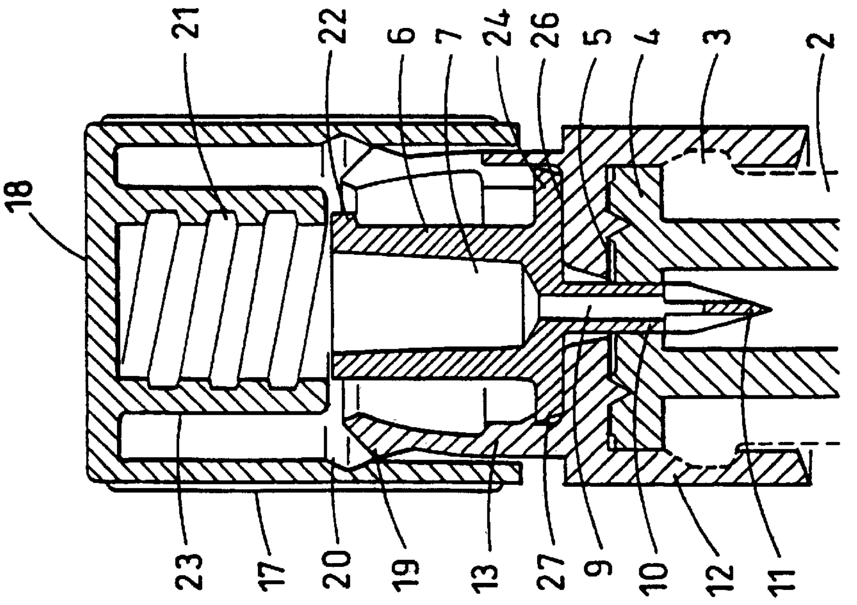
FIG. 2 shows a longitudinal section through the luer connector of FIG. 1 with its luer in its second position and the driver in place on the support.

The legs 24 also comprise abutment parts which when the luer 6 has reached the extreme end of its movement into the second position, as shown in FIG. 2 abut against the upper surface 26 of flange part 14 of the support to prevent further longitudinal movement of the luer.

The luer 6 also has legs 27 which engage in a snap-fit manner with recesses 28 on the support when the luer 6 has reached the limits of its movement into its second position as shown in FIG. 2 so that the luer is locked in place in its second position. The legs 27 also comprise further abutment parts which abut against the surface 26.

The engaging circumferential bead parts 19 and the groove 20, which allow relative rotation and guide the sleeves in smooth rotation about the axis of the sleeves whilst restraining relative axial movement, also provide a snap-fit barrier to removal of the driver 17 in the axial direction from the support 12. The screw thread parts 21, 22 are of dimensions such that when the conduit 10 has entered the vial 1 as far as is allowed by the abutment parts as shown in FIG. 2 the screw thread parts 21, 22 on the driver 17 and luer 6 are still engaged. Their continued relative rotation consequently generates an upward thrust upon the driver 17 to disengage it from the support 12 by a snap-fit disengagement of the engaging circumferential bead parts 19 and the groove 20 as shown in FIG. 2. The upper part 13 of the support 12 is resilient, and flexibility is assisted by the presence of the slots 25, facilitating the bead parts 19 to be detached from the groove 20.

To prevent accidental or unintended relative movement of the driver 17 and support 12, the support 12 and driver 17 are initially connected with a small spot weld at 29. This breaks when relative motion is intentionally applied to the driver to operate the device and also functions as tamper evidence means to detect tampering.

Figure 3:
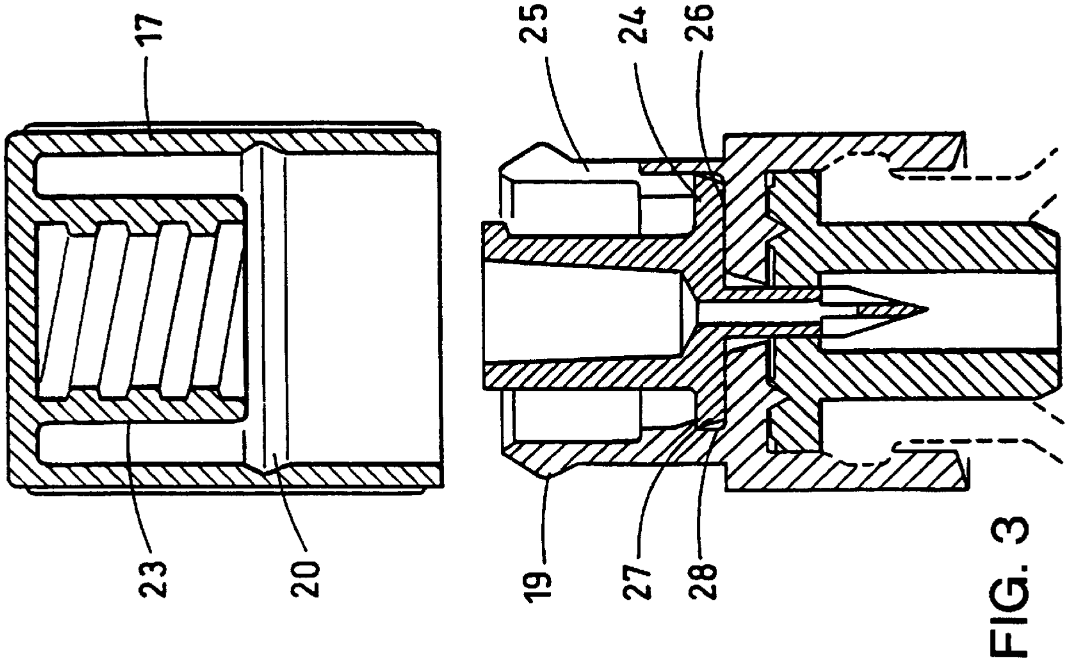
FIG. 3 shows a longitudinal section through the luer connector of FIG. 1 with its luer in its second position and the driver removed from the support.
Figure 4:
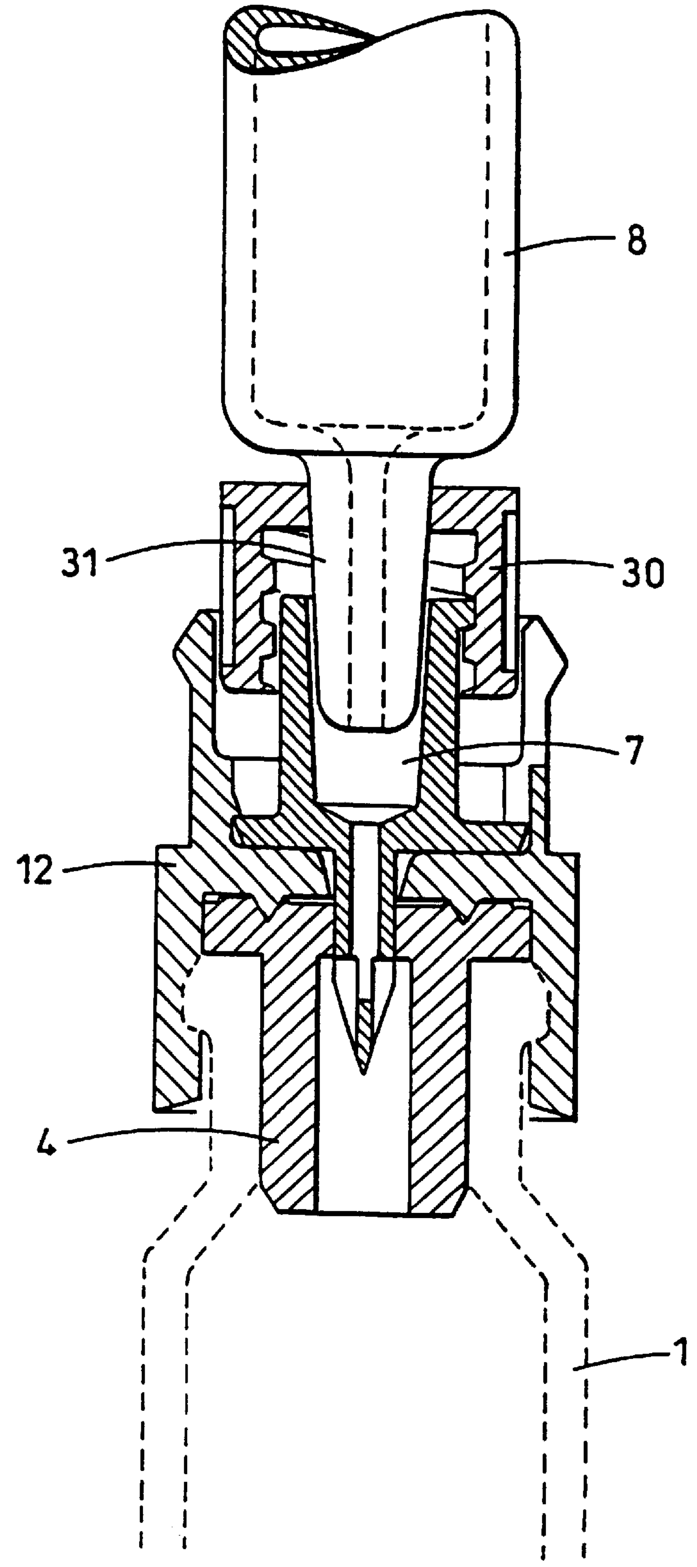
FIG. 4 shows a longitudinal section through the luer connector of FIG. 1 with its luer in its second position with the driver removed from the support, and connected to a syringe.

The operation of the luer connector of the invention is apparent from FIGS. 1 to 4. With the connector as shown in FIG. 1, with the closure 4 unpunctured, the driver 17 is rotated by a hand twisting action whilst also holding the vial 1. This causes the screw thread parts 21, 22 to engage so as to screw the luer 6 downwards, causing the pointed end 11 of the conduit 10 to puncture the closure 4 and enter the vial 1. When the luer 6 has reached the limit of its downward movement the abutment parts 24, 27 abut against flange 14 to prevent further downward movement of the luer, and the snap-fit engagement parts 27, 28 engage to lock the luer 6 into place as shown in FIG. 2. Continued rotation of the driver 17 forces the driver 17 off the support 12 against the snap-fit engagement of bead 19 and groove 20 as shown in FIG. 3. A syringe 8 may then be connected to the luer port 7, using an adapter 30 to firmly link the port and nozzle 31 of syringe 8 together if desired as shown in FIG. 4.

Referring to FIGS. 5 to 9, parts corresponding in function and operation to corresponding parts in FIGS. 1–4 are numbered correspondingly, and only differences are described in detail. In its essential principles the luer connector of FIGS. 5–9 is identical to that of FIGS. 1–4.

Figure 5:
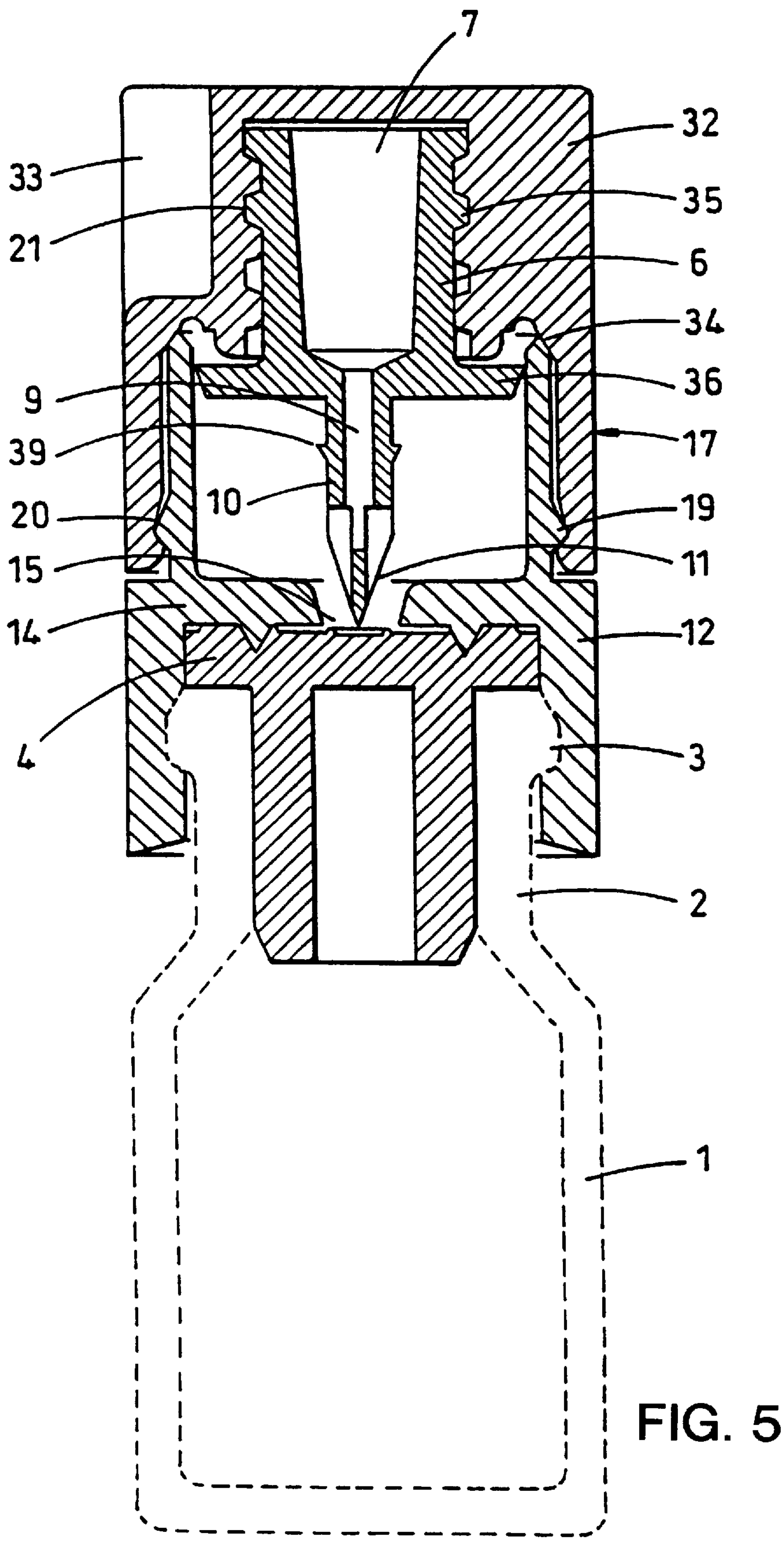
FIG. 5 shows a longitudinal section through a second type of luer connector of the invention with its luer in its first position.

In FIG. 5 the luer support 12 is again in the form of a sleeve mounted on the neck of the vial 1. The luer driver 17 is again in the form of a sleeve coaxial with the upper part 13 of the support in the manner of a skirt, and rotatable on the part 13. The driver 17 has an integral upper part 32 which is formed with ribs 33 to assist gripping by the user. The inner surface of this upper part 32 is provided with a screw thread 21. The luer support forms a sterile seal with the luer driver at the point 34, where matching conical surfaces of the uppermost lip of the part 13 and on the luer driver 17 meet and form a cone/cone surface seal. This seal may be improved by a smear of silicone.

Figure 8:
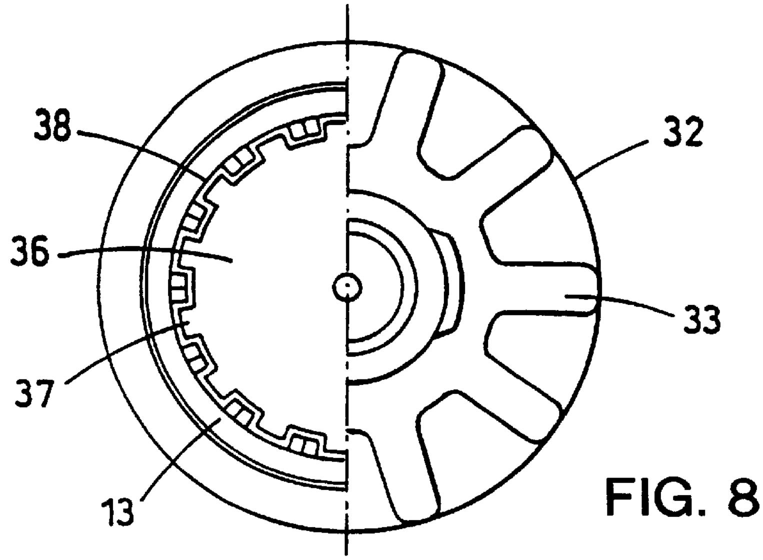
FIG. 8 shows a part cutaway plan view of the luer connector of FIG. 1.

Within the compartment 13 and the upper part 17 is located a luer 6 of similar construction to that of FIGS. 1–4. However instead of the projection 22 used in FIGS. 1–4 there is a helical thread 35 on the outer surface of the luer port 7, engaging with the thread 21. Instead of the legs 24 used in FIGS. 1–4 the luer 6 is provided with an abutment flange 36 which, as shown in FIG. 8, at its periphery is formed into a gear-tooth shape in which the teeth 37 engage with corresponding longitudinal grooves 38 on the inner surface of the compartment 13, and this engagement both guides the luer into smooth longitudinal movement down the compartment 13 and prevents relative rotation of the luer 6 and support 12.

Figure 6:
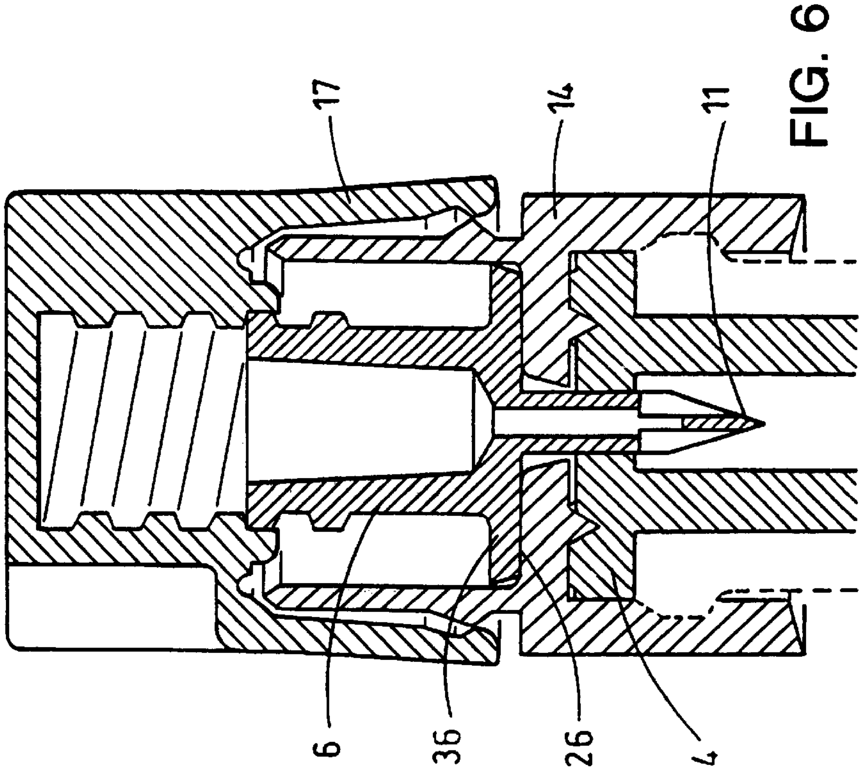
FIG. 6 shows a longitudinal section through the luer connector of FIG. 5 with its luer in its second position and the driver in place on the support.

As shown more clearly in FIG. 6, rotation of the luer driver 17 screws the luer 6 downwards in a similar manner to FIGS. 1–4, so that the sharp end 11 punctures the closure 4 and enters the vial (not shown in FIG. 6). The extent of downward movement of the luer is determined by the abutment of the abutment flange 36 against the upper surface 26 of flange part 14 of the support to prevent further longitudinal movement of the luer 6. At the same time the small wedge-shaped fins 39 on the conduit 10 engage under the flange 14 to retain the luer in place. As shown in FIG. 6 the luer 7 is in its second position.

Figure 7:
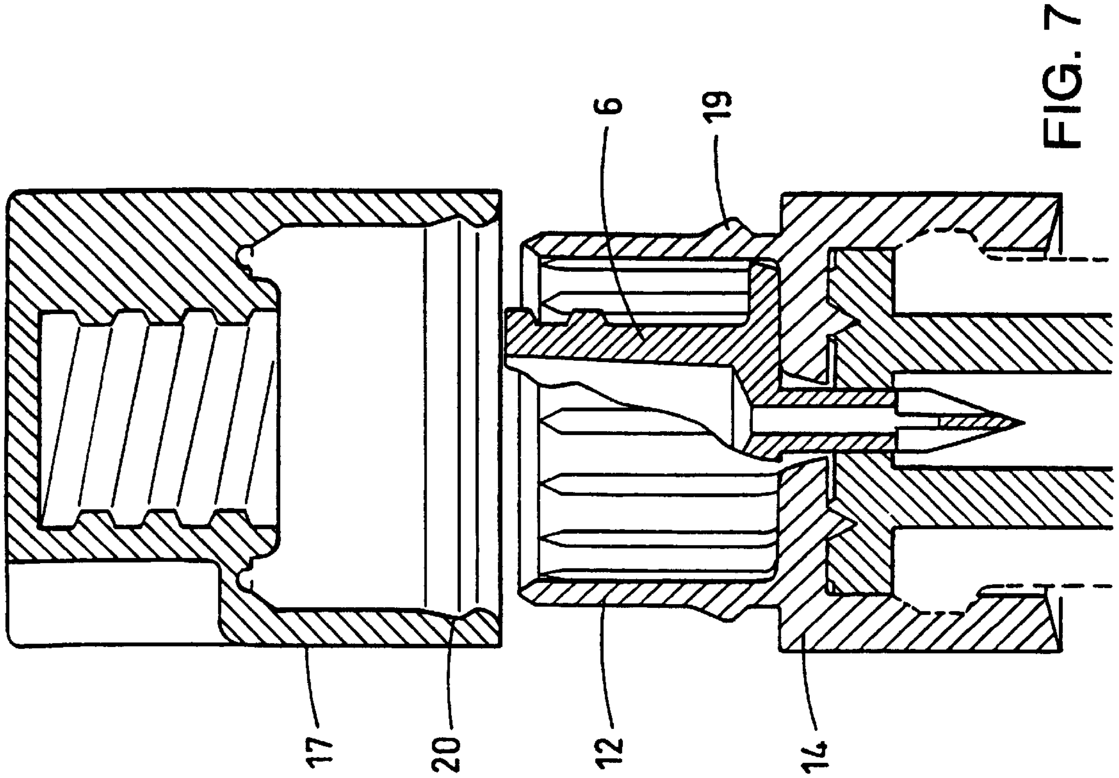
FIG. 7 shows a part cutaway longitudinal sectional view through the luer connector of FIG. 5 with its luer in its second position and the driver removed from the support.

Continued rotation of the luer driver 17 with the luer 6 abutted against flange 14 applies an upward force to the luer driver 17, and as shown in FIG. 7 forces the luer driver 17 and support 12 out of engagement until they become fully detached as shown in FIG. 7. Thereafter a syringe 8 (not shown) may be connected to the luer port 7 in an identical manner to FIG. 4.

Figure 9:
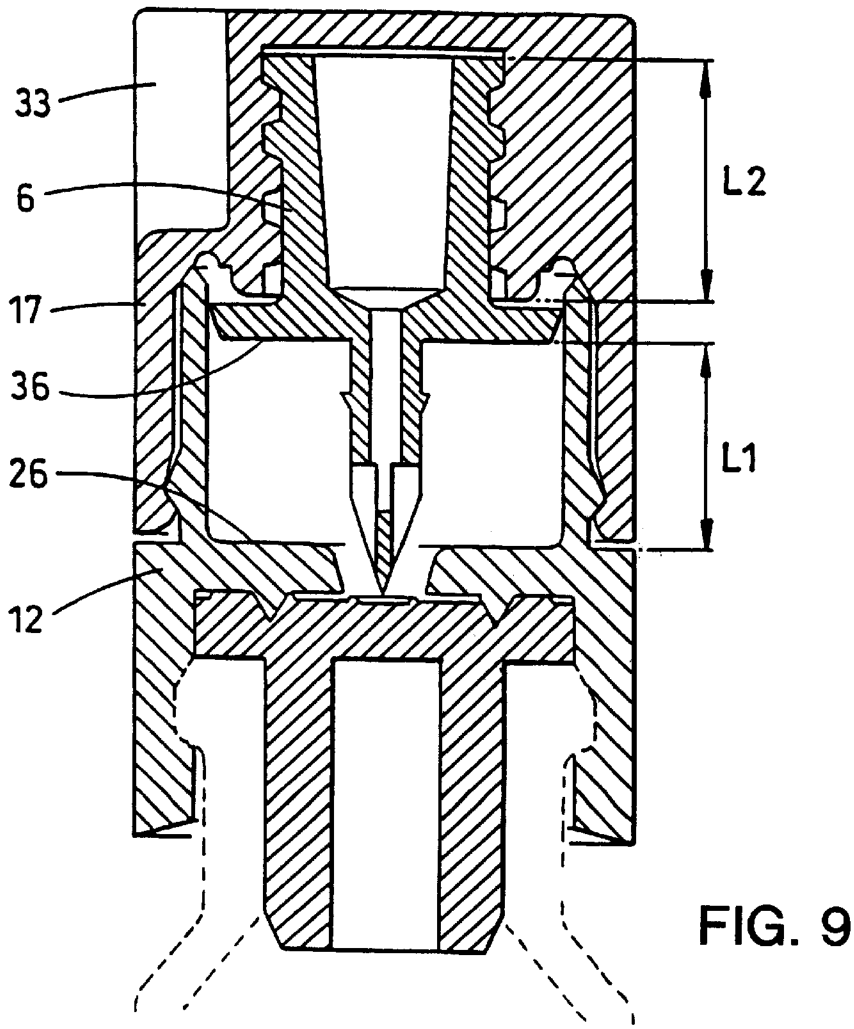
FIG. 9 shows a longitudinal section through the luer connector of FIG. 5 showing more clearly the operation of the screw thread parts.

Referring to FIG. 9 which in part reproduces FIG. 5, as described above when the luer 6 is in its first position as shown in FIG. 9 the abutment surfaces 36 and 26 are separated by a longitudinal distance L1. The longitudinal distance the luer 7 can be moved by the screw action of the luer driver 32, e.g. the longitudinal distance between the upper 40 and lower 41 ends of the screw thread 21 part on the luer driver 32 is L2, in this case corresponding to the full length of the screw thread on the luer driver 32. L2 is greater than L1 so that when the said abutment surfaces 36 and 26 are in contact the continued rotation of the luer driver 32 relative to the luer 6 continues to apply a longitudinal downward force to the luer. As the abutment surfaces prevent further downward movement of the luer this results in an upward reaction force which forces the luer driver upwards and longitudinally out of engagement with the support, allowing the luer driver 32 to become detached as shown in FIG. 7. The same principle applies to the luer connector of FIGS. 1–4.

It will be appreciated that the construction of luer connector described above can be easily provided with tamper-evidence features, for example small rupturable plastic material links between the skirt 17 and the support 12, or a tearable label that bridges the skirt 17 and the support 12, which becomes torn if the luer driver 17 is rotated relative to the skirt 12. Other types of tampler evidence construction will be apparent to those skilled in the art.

What is claimed is:

1. A luer connector which comprises;

a luer comprising a luer port connectable to a syringe and being in communication with a first end of a channel passing longitudinally through a tubular conduit, the conduit extending longitudinally from the luer port to a second end of the channel, the end of the tubular conduit remote from the luer port being sharpened so as to be capable of being driven through a puncturable vial closure to thereby puncture the closure;

a luer support, mountable on a vial when the vial is sealed with a puncturable vial closure, the support initially supporting the luer longitudinally moveable in a first position in which the sharpened end of the conduit is pointed toward the closure; characterised by;

a luer driver, rotatably moveably mounted on the support and engaged with the support, the luer and driver having engaging screw thread parts thereupon such that engagement of the screw thread parts and relative rotation of the driver and the luer causes the luer driver to bear upon the luer so as to drive the luer longitudinally into a second position in which the sharpened end of the conduit is driven through the closure to puncture the closure and to enter the vial.

2. A luer connector according to claim 1 charaterised in that, the luer is provided with one or more abutment part(s) which when the luer has reached the extreme end of its movement into the second position prevent further longitudinal movement of the luer, and the arrangement of the screw thread parts and abutment parts are such that when the conduit has entered the vial as far as is desired or allowed by the abutment part(s) the screw thread parts on the luer driver and luer are still engaged, so at their continued relative rotation generates an upward thrust upon the luer driver to force the luer driver out of engagement with the support.

3. A luer connector according to claim 1 characterised in that the luer support comprises a sleeve which is mountable around the neck of the vial, so as to be thereby retained on the neck and extends above the mouth of the vial, and the upper part of the support above the mouth of the vial is in the form of a generally tubular extension defining a compartment extending above the vial closure, and having an upper open end, of suitable dimensions that the luer can be supported therein in its first position with the sharpened end of the conduit pointed toward the closure.

4. A luer connector according to claim 1 characterised in that the luer and the support include respective engagement parts so that when the luer has reached the limits of its movement from its first to its second position, with the conduit as far within the vial as desired, the luer is locked in place in its second position.

5. A luer connector according to claim 3 characterised in that the luer driver is in the form of a closure closing the upper end of the compartment.

6. A luer connector according to claim 5 charaterised in that luer driver is in the form of a cap closing the upper open end of the compartment by means of the luer driver having a wholly closed end which forms a closure surface over the open end of the compartment.

7. A luer connector according to claim 1 characterised in that the luer is provided with means to resist rotation with the luer driver when the luer driver is rotated on the support so that relative rotation of the luer and the driver, and hence the engagement of the screw thread parts can occur.

8. A luer connector according to claim 1 characterised in that the support and luer driver have their respective facing surfaces provided with engaging circumferential bead parts and a groove, which allow rotation and guide them in rotation about the axis of the sleeves whilst restraining relative axial movement, and which are constructed that the driver is detachable from the support by a snap-fit disengagement of the bead from the groove as the driver moves in the axial direction.

9. A luer connector according to claim 1 characterised by a construction in which the luer driver and luer have respective engaging screw thread parts thereon, and in which the luer and the support are provided with respective abutment surfaces such that the lower limit of travel of the luer within the support is reached when the respective abutment surfaces abut, and in which when the luer is in its first position the respective abutment surfaces are separated by a longitudinal distance which is less than the longitudinal distance the luer driver can be moved by the screw action of the luer driver.

10. A luer connector which comprises;

a luer, connectable to a syringe, the luer comprising a luer port in communication with a first end of a channel passing longitudinally through a tubular conduit integrally extending longitudinally from luer port to a second end of the channel, the end of the tubular conduit remote from the luer port being sharpened so as to be capable of being driven longitudinally through a puncturable vial closure to thereby puncture the closure;

a luer support, comprising a sleeve which is mountable around the neck of the vial, so as to be thereby retained on the vial when sealed with a puncturable vial closure, the support extending into an upper part above the mouth of the vial in the form of a generally cylindrical compartment extending above the vial closure and forming a guide for the luer, the compartment being of suitable dimensions that the luer is supported therein longitudinally moveable in a first position in which the sharpened end of the conduit is pointed toward the unpunctured closure;

a luer driver, mounted on the support and capable of rotational movement relative to the support and luer, the driver comprising a cylindrical sleeve or part sleeve, coaxial with the said upper part of the support, the driver being in the form of a cap over the compartment in the upper part of the support, and having a wholly or partly closed end over the compartment when the driver is in place;

the luer and driver having respective screw thread engagement parts such that engagement of the screw thread parts on the said rotational movement causes the luer to be screwed downwards toward a second position in which the sharpened end of the conduit is driven through the closure to puncture the closure and to enter the vial, and the luer is provided with one or more abutment part(s) which when the luer has reached the extreme end of its movement into the second position prevent further longitudinal movement of the luer, and the dimensions of the screw thread parts are such that when the conduit has entered the vial as far as is desired or allowed by the abutment part(s) the screw thread parts on the luer driver and luer are still engaged, so that their continued relative rotation generates an upward thrust upon the luer driver to force the luer driver out of engagement with the support.

11. A luer connector which comprises;

a luer, connectable to a syringe, the luer comprising a luer port in communication with a first end of a channel passing longitudinally through a tubular conduit integrally extending longitudinally from the luer port to a second end of the channel, the end of the tubular conduit remote from the luer port being sharpened so as to be capable of being driven longitudinally through a puncturable vial closure to thereby puncture the closure;

a luer support, comprising a sleeve which is mounted and engaged around the neck of the vial, so as to be thereby retained on the vial when sealed with a puncturable vial closure, the support extending into an upper part above the mouth of the vial in the form of a generally cylindrical compartment extending above the vial closure and forming a guide for the luer, the compartment being of suitable dimensions that the luer is supported therein longitudinally moveable in a first position in which the sharpened end of the conduit is pointed toward the unpunctured closure;

a luer driver, mounted on the support and capable of rotational movement relative to the support and luer, the driver comprising a cylindrical sleeve or part sleeve, coaxial with the said upper part of the support, the driver being in the form of a cap over the compartment in the upper part of the support, and having a wholly or partly closed end over the compartment when the driver is in place;

the luer and driver having respective screw thread engagement parts such that engagement of the screw thread parts on the said rotational movement causes the luer to be screwed downwards toward a second position in which the sharpened end of the conduit is driven through the closure to puncture the closure and to enter the vial;

the luer and the support being provided with respective abutment surfaces such that the lower limit of travel of the luer within the support is reached when the respective abutment surfaces abut, and in which when the luer is in its first position the respective abutment surfaces are separated by a longitudinal distance which is less than the longitudinal distance the luer driver can be moved by the screw action of the luer driver, so that when the abutment surfaces on the luer abuts against the abutment surface on the luer support the luer has reached the lower limit of its travel relative to the support it has not yet reached the lower limit of travel on the screw thread on the luer driver and the continued rotation of the luer driver relative to the luer will force the luer driver and support are forced longitudinally out of engagement with each other.

12. A pharmaceutical vial having a puncturable closure sealing its mouth opening, the vial being mounted with a luer connector as claimed in claims 1, 10 or 11.

* * * * *